(12) United States Patent
Osman

(10) Patent No.: US 8,636,806 B2
(45) Date of Patent: Jan. 28, 2014

(54) BIOLOGIC DIARTHRODIAL JOINT

(76) Inventor: Said G. Osman, Frederick, MD (US)

(*) Notice: Subject to any disclaimer, the term of this patent is extended or adjusted under 35 U.S.C. 154(b) by 0 days.

(21) Appl. No.: 13/499,783

(22) PCT Filed: Oct. 4, 2010

(86) PCT No.: PCT/US2010/051307
§ 371 (c)(1),
(2), (4) Date: Apr. 2, 2012

(87) PCT Pub. No.: WO2011/041774
PCT Pub. Date: Apr. 7, 2011

(65) Prior Publication Data
US 2012/0203341 A1 Aug. 9, 2012

Related U.S. Application Data (60) Provisional application No. 61/248,088, filed on Oct. 2, 2009.

(51) Int. Cl.
*A61F 2/30* (2006.01)
*A61F 2/28* (2006.01)

(52) U.S. Cl.
USPC ............. 623/18.11; 623/11.11; 623/16.11

(58) Field of Classification Search
CPC ........................................ A61F 2/28
USPC ................. 623/11.11, 14.12, 16.11
See application file for complete search history.

(56) References Cited

U.S. PATENT DOCUMENTS

| | | | |
|---|---|---|---|
| 5,306,311 A | 4/1994 | Stone et al. | |
| 5,314,478 A * | 5/1994 | Oka et al. | 623/14.12 |
| 6,132,468 A | 10/2000 | Mansmann | |
| 2002/0022884 A1 | 2/2002 | Mansmann | |
| 2005/0245938 A1* | 11/2005 | Kochan | 606/92 |
| 2007/0031470 A1 | 2/2007 | Kladakis et al. | |
| 2008/0097605 A1 | 4/2008 | Pastorello et al. | |
| 2008/0097606 A1* | 4/2008 | Cragg et al. | 623/14.12 |
| 2008/0288081 A1 | 11/2008 | Scrafton et al. | |
| 2009/0125115 A1 | 5/2009 | Popoola et al. | |
| 2009/0240337 A1 | 9/2009 | Myung et al. | |

FOREIGN PATENT DOCUMENTS

EP 1 208 819 5/2002

OTHER PUBLICATIONS

Supplementary European Search Report dated Jan. 30, 2013 issued in European Patent Application No. 10821396.8, 3 pp.

* cited by examiner

*Primary Examiner* — Jason-Dennis Stewart
(74) *Attorney, Agent, or Firm* — Nixon & Vanderhye P.C.

(57) ABSTRACT

A biologic diarthrodial joint includes an artificial subchondral bone shaped in the form of a joint replacement member and formed of an artificial fiber material. The artificial fiber material includes synthetic fibers formed in a fibrous network with the synthetic fibers arranged in multiple orientations. The artificial subchondral bone includes a polymer receiving component. An artificial cartilage polymer is cooperable with the artificial subchondral bone and engages the polymer receiving component. The artificial cartilage polymer has physical properties similar to that of native articular cartilage.

11 Claims, 5 Drawing Sheets

BIOLOGIC DIARTHRODIAL JOINT

CROSS-REFERENCES TO RELATED APPLICATIONS

This application claims the benefit of U.S. Provisional Patent Application Ser. No. 61/248,088, filed Oct. 2, 2009.

BACKGROUND OF THE INVENTION

Surgical techniques for painful arthritic joints have evolved through various stages over the last three centuries. The methods have involved breaking the bones and realigning them to redistribute joint forces to the less affected section of the joint; inter-position of soft tissue in between the arthritic bone surfaces; removal of the arthritic joint; fusion of the joint to eliminate pain; partial and total joint replacement. The majority of the artificial joints for the different regions of the body involve a metal alloy articulating with a plastic or ceramic component. Recently there has been a resurgence of interest in metal-on-metal artificial hip replacement.

The major issues with most of the current materials include loosening of the components; wear-and-tear debris causing foreign body reactions; breakages of the components; ions released from the metal alloys. The metal alloys have a significant drawback because of relative stiffness as compared to bone in which they are implanted, which leads to loosening over a period of time necessitating revisions. There is a progressively diminishing bone stock with successive revisions.

SUMMARY OF THE INVENTION

The current invention avoids metal alloys, ultra-high molecular weight polyethylene, and currently used ceramics. Instead, it uses implants which are biologically compatible, durable and with physical properties comparable to the host bone and cartilage. Over time, the components may or may not be partially replaced by the host tissue in-growth. The joint surfaces are polymers which have similar physical properties as native cartilage. The artificial subchondral bone (ASB) is firmly attached to the artificial cartilage. The artificial subchondral bone may be fully formed and rigid prior to implantation, or may be rendered hard after implantation by injecting bone glue, ceramic or other material. The artificial joint components may come separately or as part of artificial skeleton. The artificial joint components may come attached together by artificial stabilizing ligaments.

In an exemplary embodiment, a biologic diarthrodial joint includes an artificial subchondral bone shaped in the form of a joint replacement member and formed of an artificial fiber material. The artificial fiber material includes synthetic fibers formed in a fibrous network with the synthetic fibers arranged in multiple orientations. The artificial subchondral bone includes a polymer receiving component. An artificial cartilage polymer is cooperable with the artificial subchondral bone and engages the polymer receiving component. The artificial cartilage polymer has physical properties similar to that of native articular cartilage. The polymer receiving component may include projecting fibers of the synthetic fibers projecting from a surface of the artificial subchondral bone, either in loops or as free endings. Alternatively, or additionally, the polymer receiving component may include a plurality of crevices in a surface of the artificial subchondral bone.

In one arrangement, the artificial cartilage polymer is engaged with the artificial subchondral bone prior to implantation of the joint. The artificial cartilage polymer may be anhydrous. The artificial subchondral bone may include a cartilage space cooperable with the polymer receiving component, and the artificial cartilage polymer is injected into the cartilage space after implantation of the joint.

A stiffness of the artificial subchondral bone may be adjustable based on a density of the synthetic fibers.

In another exemplary embodiment, a method of preparing a biologic diarthrodial joint includes the steps of (1) providing an artificial subchondral bone shaped in the form of a joint replacement member and formed of an artificial fiber material, the artificial fiber material including synthetic fibers formed in a fibrous network with the synthetic fibers arranged in multiple orientations, wherein the artificial subchondral bone includes a polymer receiving component; and (2) bonding an artificial cartilage polymer to the artificial subchondral bone via the polymer receiving component, the artificial cartilage polymer having physical properties similar to that of native articular cartilage. The bonding step may be practiced prior to implantation of the joint. Alternatively, the bonding step may be practiced after implantation of the joint. In this context, the method may further include providing the artificial subchondral bone with a cartilage space cooperable with the polymer receiving component, and securing the artificial subchondral bone to a host bone, where the bonding step comprises injecting the artificial cartilage polymer into the cartilage space.

BRIEF DESCRIPTION OF THE DRAWINGS

These and other aspects and advantages will be described in detail with reference to the accompanying drawings, in which.

DETAILED DESCRIPTION OF THE INVENTION

Figure 4:
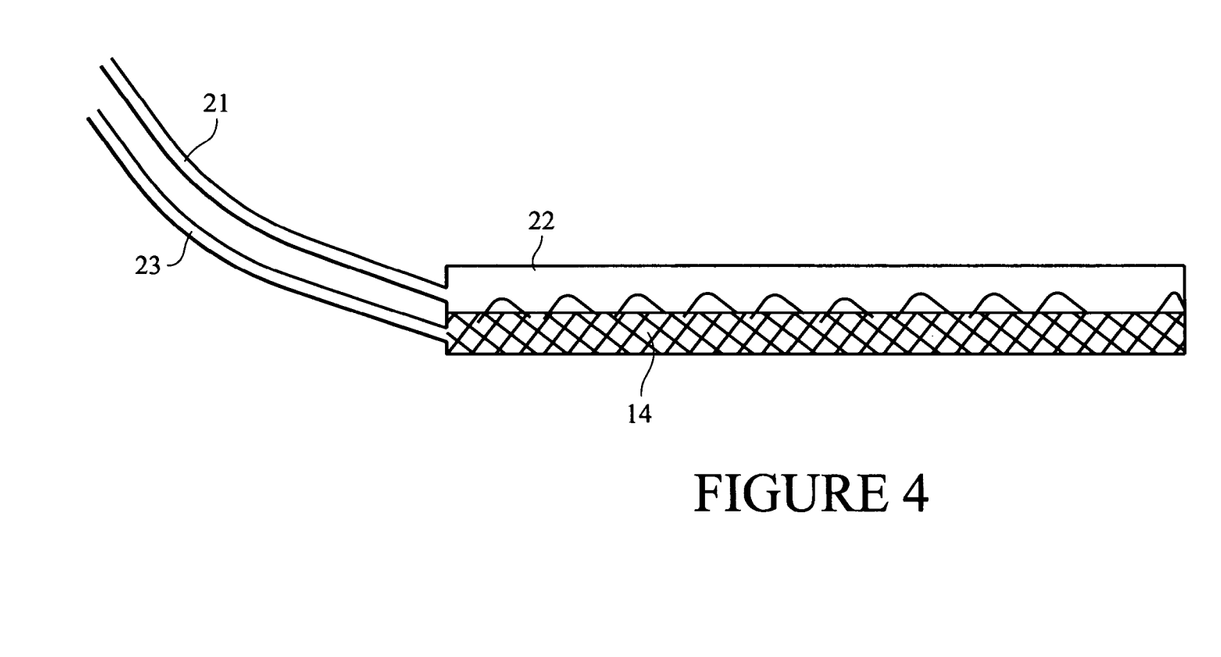
FIG. 4 shows a cartilage space delimited by an articular surface of polymer material.
Figures 5, 6:
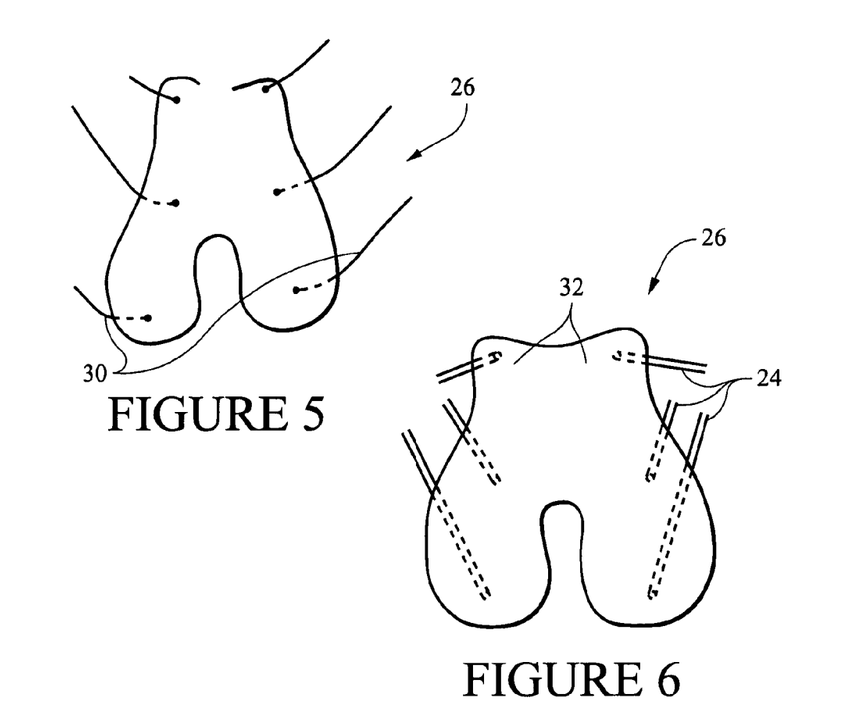
FIGS. 5-8 illustrate an application of arthroscopic peripheral joint replacement for total knee replacement.
Figure 7:
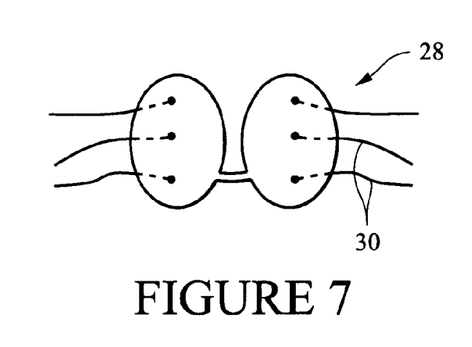
Figure 8:
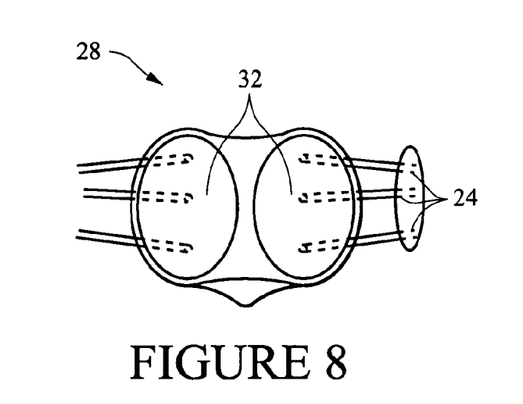
Figure 9:
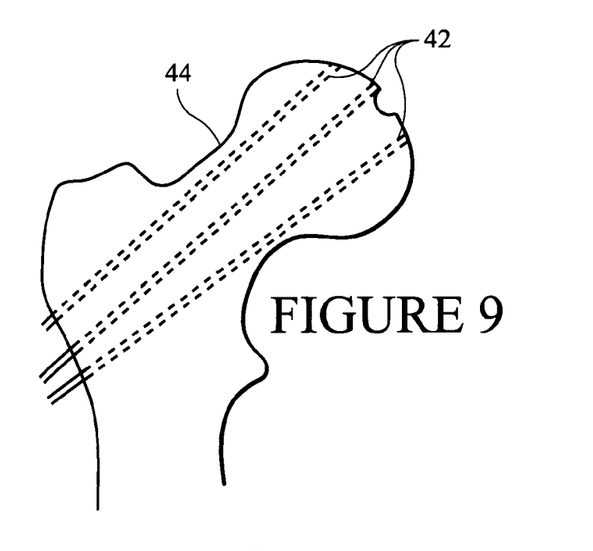
FIGS. 9-13 show an application of arthroscopic peripheral joint replacement for total hip replacement.
Figure 10:
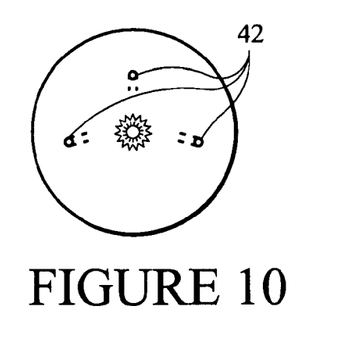
Figure 11:
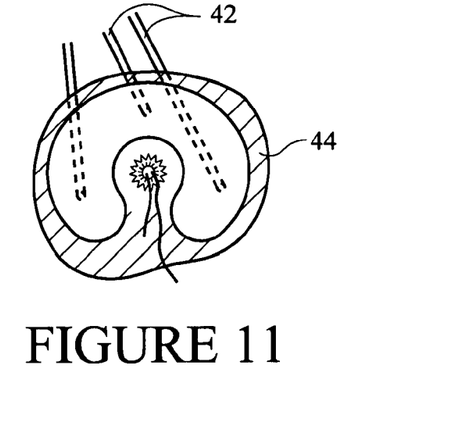
Figure 12:
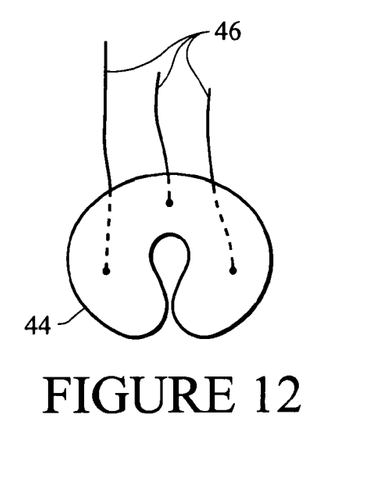
Figure 13:
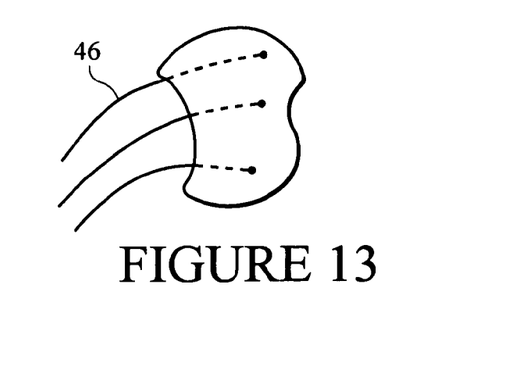

1. Articular Cartilage
   a. Artificial cartilage polymer: With reference to FIGS. 1-4, the artificial articular cartilage 12 is made of a polymer or co-polymer with physical properties similar to that of native articular cartilage. The polymer may have the osmotic property similar to that of the articular cartilage or may be osmotically inactive. The osmotically active polymer or co-polymer will absorb water from the surrounding tissues to reach equilibrium with the surrounding tissues, which will impart a shock-absorbing quality. When physiologic pressure is applied (as in weight bearing), the combined effect of the osmotic pressure and mechanical pressure may be such that liquid is squeezed out of the polymer, until a new equilibrium is established. The articular cartilage polymer 12 or co-polymer may be constructed in many ways:
      i. Pre-formed: The polymer may be incorporated into the composite of the artificial joint 10 prior to implantation in a manner similar to current practice of artificial joint construction. In this embodiment, the polymer 12 may be synthesized separately and glued to the artificial subchondral bone (ASB) 14 during the manufacture, or bonded to the subchondral bone via fibrous extensions 16, 18, which protrude from the subchondral surface. In yet another embodiment, the polymer in semi-liquid state may be poured into crevices 20 in the sub-chondral surface so that the ASB 14 and the polymer 12 may interlock strongly. In yet another embodiment, the artificial articular cartilage is not backed with artificial subchondral bone but a layer of material which will facilitate bonding to the underlying host bone via mechanisms which include, but are not limited to, a form of glue, bone anchor, osteogenic factor, and combinations thereof.

ii. Pre-formed and implanted in anhydrous form: The osmotically active artificial cartilage 12 (e.g., hydrogel) may be manufactured in the manner described above but may be kept anhydrous (dry), but after implantation, the polymer 12 will imbibe fluid from the surrounding tissues and gain properties similar to that of the native articular cartilage.

iii. Polymer injected into the artificial cartilage space and polymerization taking place in situ: In yet another embodiment, the polymer 12 is injected via an injection channel 21 into a cartilage compartment 22, which may or may not have the subjacent artificial sub-chondral bone 14. In this embodiment, the device is produced to conform to the geometry of the bone end to be covered, but it is not armed with the polymer; instead, a cartilage space 22 delimited by an articular surface of bioabsorble or nonabsorbable polymer material, and the osseous surface of nonabsorbable/absorbable layer of fabric or ASB (artificial subchondral bone) not stiffened with bone substitute until after implantation. The bone substitute is injected into the fabric matrix via an injection channel 23. Once implantation of the device has been performed, the polymer is injected into the cartilage space 22, and bone ceramic may be injected into the ASB to stiffen it and glue it to the host bone. Other techniques including different methods of anchoring of the prosthesis may be used separately or in conjunction with ones described above.

b. Binding the Polymer to the Subchondral Bone i. Loops from the subchondral bone extending into the cartilage space:

The artificial subchondral bone 14 is produced in the manner previously described in U.S. patent application Ser. No. 11/955,684. As described therein, a base material is constructed of an artificial fiber to replace the collagens in bone. This fiber could be made from various synthetic polymers whose mechanical properties are similar to or stronger than type I collagen. The polymer matrix framework could be made into a cast in the shape of various bones, or the implants currently used to fix fractures.

In one embodiment, the fibers of the base material may be in the pattern of a network with fibers arranged in horizontal, vertical and oblique orientations, such that the base material is able to impart tensile, shear, bending and compressive strength to the final composite. In another embodiment, the polymer matrix framework can be made in a concentric cylindrical arrangement with several cylinders, depending on the load to which the bone or implant will be subjected. The cylinders may be made in the shape of specific bone or implant, and the structure is thus suitable as an intra-medullary rod, or artificial joint. The cylinders are composed of fibers in vertical, horizontal and spiral arrangements to meet the demands of various stresses to which the bone is subjected. In another embodiment, adjacent cylinders are interconnected by transverse fibers running across all the cylinders in the same planes or in staggered fashion or a mixture of both.

In still another embodiment, the polymer matrix framework is made with a horizontal, vertical and spiral fiber network in the form of a sheet which is then rolled into a multi-layered cylinder. The center of a long bone is made relatively empty and may be used for insertion of a morphogenic factor such as hemopoietic factors to facilitate population of the construct with blood forming cells. The growth factor may be implanted as the inner layer of long bone to mimic the endosteum and on the outer wall to mimic the periosteum to induce recruitment of osteo-genic bone on both surfaces of the artificial device.

The ends of the long bones, in another embodiment, include cylindrical fibers of lesser thickness than the cortical shaft bone, but a there is a dense network of fibers throughout its width to resemble the metaphysic and the epiphysis of the long bone. This network will, in a later stage of processing, be impregnated with ceramic bone to impart physiologic resistance to compressive forces. For the attachment of tendons and ligaments, a stump of the polymer fibers, continuous with the matrix of the artificial bone, is developed at the anatomical sites of the artificial bone, for the insertions or origins of these structures.

Numerous mechanisms may be utilized to maintain the shape of the artificial bone or implant, such as the intramedullary rod. In one embodiment, while maintaining the shape of the construct on a mold, the fabric may be impregnated with a biocompatible, fast curing liquid substance which hardens and stiffens the construct as it dries, thereby allowing it to maintain the desired shape. Alternatively, the fabric itself may be manufactured at such a temperature that as it cools or warms up it hardens, thereby retaining the shape of the mold. Still further, the fabric may be maintained in the desired shape inside, outside or sandwiched within the wall of the mold, and impregnated with a stiffening substance.

The polymer matrix so constructed can then be impregnated with bone substitute such as ceramics. In one embodiment, the composite, with the polymer fabric in the shape of the bone or desired implant, may be formed by immersion into a mold containing ceramic in liquid form and allowed to set by altering the temperature. Alternatively, the polymer fabric may be placed in the mold and the ceramic poured into the mold and allowed to set incorporating the polymer matrix framework. The polymer matrix framework in the form of the desired structure may be sprayed with the ceramic bone substitute which then hardens to the stiffness of bone as it sets. The polymer matrix framework in the form of the desired device may alternatively be grit-blasted with the bone ceramic. Still further, the cylinders of the device may be individually impregnated with the ceramic, and the cylinders so formed may then be inserted into each other and bonded together via the ceramic layers. In a preferred embodiment, the polymer sheet is rolled into a cylinder to produce the desired device, and the device is then impregnated with the ceramic using any one of the methods described above. Once impregnated, the polymer fabric becomes an artificial bone composite.

In order for the remodeling of the artificial bone or implant to occur expeditiously, channels may be created in the artificial bone composite, and the channel walls may be coated with angiogenic factors to facilitate in-growth of vessels and bone forming cells. The vascular channels may be created in any suitable manner.

In one embodiment, the polymer fiber matrix in the shape of the desired bone or implant is made of a fine network of fibers with variable dimensions of spaces between the fibers depending on the function of the bone or device as described above. The device is then placed on a mold and hardened by immersion in, or spraying with a substance that hardens with cooling or heating. The structure is then sprayed with liquid ceramic bone substitute. The composite will have porosity of variable amounts depending on the function for which it is intended.

Figure 1:
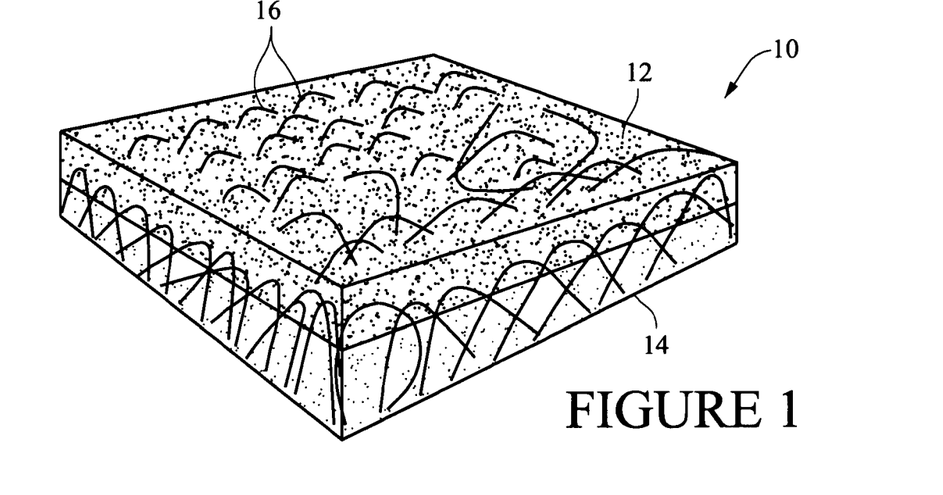
FIG. 1 is a perspective view of the joint showing synthetic fibers of the artificial subchondral bone projecting through the subarticular surface in loops.
Figure 2:
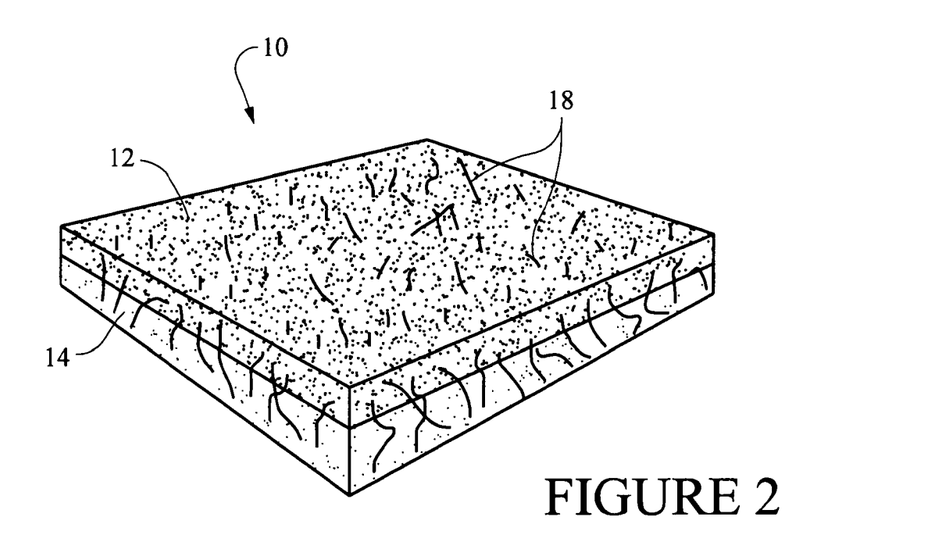
FIG. 2 shows the synthetic fibers projecting through the subarticular surface as free ends.
Figure 3:
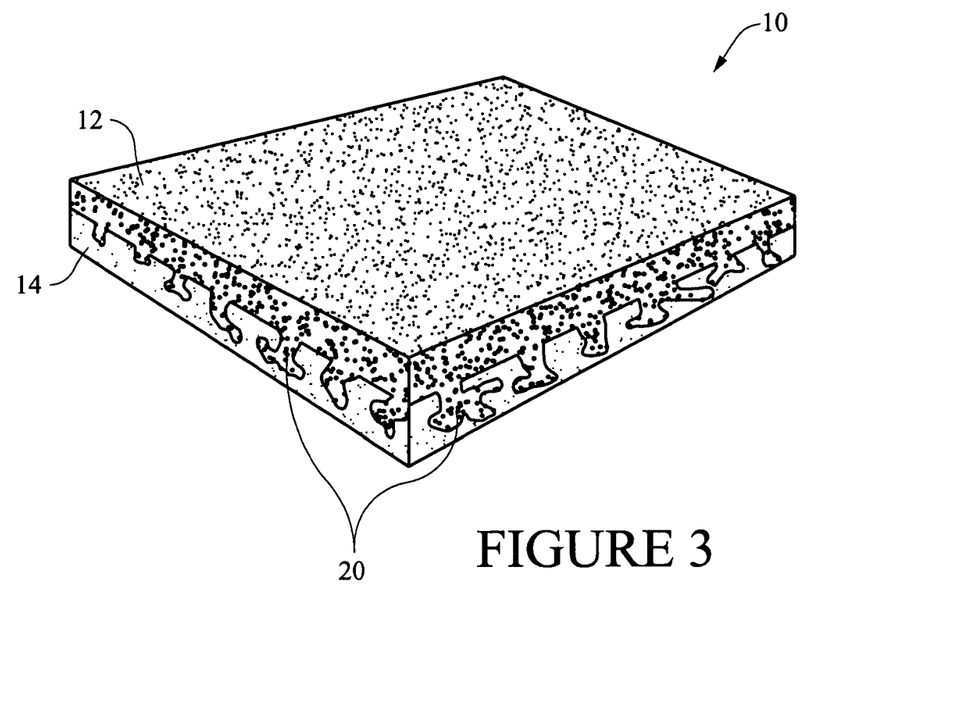
FIG. 3 shows the surface of the artificial subchondral bone including crevices.

Alternatively, at the time of manufacture, the polymer matrix framework may be wrapped with a porous sheet of absorbable material which has spikes of variable density on different areas of its surface. The sheet is wrapped around the fiber framework such that the surface containing the spikes is adjacent the fiber framework. The sheet is wrapped such that the spikes penetrate into the framework. The ceramic in liquid or molten form is then applied to the framework using any of the above embodiments. The sheet material may be removed by various techniques once the composite has hardened. Removal of the spikes and the sheet may include dissolution in appropriate chemical, heating, or in vivo dissolution in body fluid.

ii. The strong synthetic fibers used as the fibrous matrix of the bone are allowed to project from the surface of the artificial subchondral bone in loops 16 or as free endings 18. These fibers may cover the artificial subchondral bone surface densely or sparsely depending on the binding properties of the polymer on to the sub-chondral bone surface. The polymer 12 is then added to the surface of the ASB (artificial subchondral bone) 14 where it flows through the fibrous layer, incorporating the latter into its solid fabric, rendering the polymer inseparable from the ASB.

iii. Polymer filling in the crevices in the subchondral bone and bindings: The surface of the ASB may be designed with plurality of crevices 20. The polymer 12 in a liquid form may be used to cover the articular surface of the ASB 14. The polymer may flow into the crevices 20 and create an unyielding bond between the two.

iv. Combination of the Above

2. Artificial Subchondral bone: The artificial subchondral bone is produced in the manner described in the above-noted U.S. patent application. The density of the synthetic fibers may be increased and the density of calcium compound used to stiffen the bone may be more, to withstand the forces to which the artificial joint 10 is subjected. As noted, the biologic artificial bone includes channels for in-growth of vessels and host bone. The synthetic fibers are made to project through the subarticular surface in loops 16 or free ends 18 as illustrated in FIGS. 1 and 2. Alternatively, the surface of the subchondral bone 14 may be armed with plurality of crevices 20 to receive the polymer 12 in liquid form for firm bonding between the ASB and the artificial cartilage. The composite of the subchondral bone and the polymer may be produced in yet another embodiment where the ASB is not impregnated with stiffener or calcium salt. In this embodiment, the space for the polymer is covered with dissolvable material. Through a portal, the polymer may then be injected into the pocket covering the artificial subchondral bone, after the latter has been implanted into the patient. This embodiment is particularly suitable for arthroscopic joint replacement and for minimal incision joint replacement.

3. Fixation of the artificial joint to the host bone: The fixation of the artificial joint components 10 to the host bone may be performed in the manners currently practiced in the art. This may involve some form of bone glue, pegs or screws. The technique of hip socket fixation has been described in the noted U.S. patent application. For arthroscopic joint replacements where flexible prostheses are first implanted before injection of the polymer and calcium compounds, any number of special techniques of implantation and fixation of the device may be necessary. This may involve bioabsorbable staples, pegs, screws, trans-osseous suture fixation and any other device of fixation. The trans-osseous and/or transarticular fixation sutures may also be used to place the prosthesis in the intra-articular space and drape the prosthesis on the articular surfaces of the bones forming diarthrodial joints.

4. Artificial joints—The following are examples of the artificial joint replacement which can be practiced in the manners described above:

a. Hip joint
    b. Knee joint
    c. Shoulder joint
    d. Ankle joint
    e. Elbow joint
    f. Wrist joints
    g. Joints of the hand and feet
    h. Spinal joints 5. Other Applications of the Invention     a. Partial joint replacement, as in hemi-arthroplasty. In this embodiment, the joint component will be part of the biologic femoral component.
    b. Unicompartmental joint replacement in the knee.
    c. Filling defects in the articular surface of any joint as in the case of osteochondritis dessicans and osteochondral fractures with significant loss of articular surface.
    d. As articular surface of biologic bones used to replace host bone, as in replacement of parts destroyed by malignant lesions, infections or traumatic bone loss.

Method of Application of the Device:

1. Conventional open techniques: The approaches practiced here are once currently used in joint replacement.

2. Minimal incision techniques: Currently minimal incision surgery is gaining in popularity for hip and knee replacement.

3. Least invasive—arthroscopic technique. No method currently exists for arthroscopic replacement of a major peripheral joint. The prerequisites for such a procedure include but are not limited to the following:

a. Thorough knowledge of the articular and periarticular anatomy
    b. Surgeon's competence in open joint replacement, should conversion to conventional technique become necessary
    c. The accessibility of the joint compartment(s) for thorough excision and preparation of the bone surfaces
    d. Minimal deformation of the joint surfaces
    e. Stability of the joint—i.e. competent joint stabilizing ligaments.
    f. Good quality bone for trans-osseous fixation of the prosthesis 4. Techniques for Athroscopic Peripheral Joint Replacement:

a. Total knee replacement:
        i. Establish the anterolateral and anteromedial portals for diagnostic arthroscopy and debridement of articular surfaces of the femur, tibia and patella.
        ii. Establish additional portals supero-laterally and supero-medially for additional preparation of the articular surfaces and debridement of the suprapatellar pouch and the lateral and medial gutters. These portals will also serve for the insertion of the prosthesis into the joint. Additional portals may be necessary postero-laterally and postero-medially.

iii. Remove all the debris from the medial and lateral compartments.

iv. Remove the articular cartilage down to the subchondral bone. Remove as much of the subchondral as is recommended by the manufacturer for the application of the prosthesis.

v. With reference to FIGS. 5-8, under fluoroscopic or other navigation system, drill holes 24 into the femoral articular surfaces 26, the tibial articular surfaces 28 and the patellar articular surface for the insertion of the anchoring sutures 30. The holes should be strategically placed on the articular surfaces 32 such that threads passed through them and attached to the specific locations on the prosthesis can be used to pull the prosthesis accurately into place over the articular surface of the target bone.

vi. Insert a suture guide into the holes to exit the guide into the joint.

vii. Pass suture lasso into the joint through the guide to exit into the joint. Remove the guide.

viii. Through an appropriate portal, pass a suture grasper and pull the lasso into the portal.

ix. Pass the end of the appropriate thread attached to the prosthesis and pull it through the hole in the bone and out through the portal.

x. Pass all the threads though the bone as described above.

xi. Repeat the procedures for the other condyle.

xii. Pull on specific threads to transfer the prosthesis into the joint.

xiii. Pull on specific threads to drape the prosthesis on the bone end. Arthroscopically assist in the placement of the prosthesis in proper position.

xiv. Fasten the threads on the bone by a variety of methods currently in practice.

xv. Inject the bone glue into the artificial subchondral bone compartment to glue the prosthesis to the bone.

xvi. Inject the polymer into the articular cartilage compartment.

xvii. Range the joint through full flexion and extension motions to ensure appropriate distribution of the polymer in the cartilage compartment before it polymerizes into a firm consistency.

b. Total Hip Replacement:

i. Patient may be placed in supine or lateral position on a fracture table or some variation of standard operating table.

ii. The hip may be placed in traction either through a traction boot on the fracture table or variation thereof, or through a distractor fixed to the pelvis and femur.

iii. The standard arthroscopic portals—anterior, anterolateral, and posterolateral, and additional portals may be used for access to the hip joint. Separate anchor sites may be used to for the fixation of the acetabular component of the hip prosthesis.

iv. Preliminary capsular release may be necessary to facilitate opening up of the joint space under traction. This may be performed extra-articularly (using soft tissue endoscopy technique) or intra-articularly.

v. The standard portals, or variations thereof, may be used for the excision of the joint surfaces of the femoral head and the acetabulum.

vi. The preparation of the articular surfaces may be performed under arthroscopic visualization and navigation system, to guide appropriate amount of excision, especially in the cases of severely deformed joints.

vii. Irrigation and suction systems may be used to clear the debris from the joint.

viii. With reference to FIGS. 9-13, under fluoroscopic or navigation guidance, the anchor holes 42 may be prepared in the acetabulum 44.

ix. Suture lassos 46 are passed through the appropriate portals and brought out through the prosthesis implantation portal.

x. The appropriate prosthesis anchor is attached to the appropriate lasso and pulled out through the appropriate acetabular anchor hole.

xi. The prosthesis is pulled into place using the anchor threads, and position is adjusted arthroscopically using appropriate instruments.

xii. The prosthesis is then injected with the bone fixation material, and the polymer as described for the knee arthroplasty. The injections may be deferred until after the implantation of the femoral component.

xiii. The femoral head anchor holes 42 may be performed under fluoroscopic/navigation system control.

xiv. Lassos 46 are passed into the joint through the anchor holes.

xv. Appropriate prosthesis threads are attached to the appropriate lassos and the lassos are pulled back pulling the femoral component into the joint.

xvi. Adjustment of the femoral component position is performed arthroscopically using the various arthroscopic instruments.

xvii. The anchoring threads are then fixed using any methods currently in practice.

xviii. The injection channels are used to inject the subchondral—prosthesis to bone fixation material—e.g., bone glue such as biologically incorporable bone cement; and the polymer for the artificial cartilage.

xix. The injection channel may be sealed by any method currently in practice.

c. By variation of current approaches to all joints—mainly by modifying portal sites, sizes and the number of portals, the joint debridement, implantation surface preparation, and implantation of the artificial joint may be performed in all peripheral joints which are candidates for conventional joint replacements.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A biologic diarthrodial joint comprising:
an artificial subchondral bone shaped in the form of a joint replacement member and formed of a biologically compatible non-metallic artificial fiber material, the artificial fiber material including synthetic fibers formed in a fibrous network with the synthetic fibers arranged in multiple orientations, wherein the artificial subchondral bone includes a polymer receiving component, the polymer receiving component including at least one of projecting fibers of the synthetic fibers projecting from a surface of the artificial subchondral bone and a plurality of crevices in a surface of the artificial subchondral bone; and an artificial cartilage polymer cooperable with the artificial subchondral bone and engaging the polymer receiving component, the artificial cartilage polymer having physical properties similar to that of native articular cartilage.

2. A biologic diarthrodial joint according to claim 1, wherein the projecting fibers project from the surface of the artificial subchondral bone in loops.

3. A biologic diarthrodial joint according to claim 1, wherein the projecting fibers project from the surface of the artificial subchondral bone as free endings.

4. A biologic diarthrodial joint according to claim 1, wherein the artificial cartilage polymer is engaged with the artificial subchondral bone prior to implantation of the joint.

5. A biologic diarthrodial joint according to claim 1, wherein the artificial cartilage polymer is anhydrous.

6. A biologic diarthrodial joint according to claim 1, wherein the artificial subchondral bone comprises a cartilage space cooperable with the polymer receiving component, and wherein the artificial cartilage polymer is injected into the cartilage space after implantation of the joint.

7. A biologic diarthrodial joint according to claim 1, wherein a stiffness of the artificial subchondral bone is adjustable based on a density of the synthetic fibers.

8. A method of preparing a biologic diarthrodial joint, the method comprising:
   providing an artificial subchondral bone shaped in the form of a joint replacement member and formed of a biologically compatible non-metallic artificial fiber material, the artificial fiber material including synthetic fibers formed in a fibrous network with the synthetic fibers arranged in multiple orientations, wherein the artificial subchondral bone includes a polymer receiving component;
   forming the polymer receiving component by at least one of projecting fibers of the synthetic fibers from a surface of the artificial subchondral bone and forming a plurality of crevices in a surface of the artificial subchondral bone; and
   bonding an artificial cartilage polymer to the artificial subchondral bone via the polymer receiving component, the artificial cartilage polymer having physical properties similar to that of native articular cartilage.

9. A method according to claim 8, wherein the bonding step is practiced prior to implantation of the joint.

10. A method according to claim 8, wherein the bonding step is practiced after implantation of the joint.

11. A method according to claim 10, further comprising providing the artificial subchondral bone with a cartilage space cooperable with the polymer receiving component, and securing the artificial subchondral bone to a host bone, wherein the bonding step comprises injecting the artificial cartilage polymer into the cartilage space.

* * * * *